US012760335B2

(12) United States Patent
Go et al.

(10) Patent No.: US 12,760,335 B2
(45) Date of Patent: Oct. 13, 2026

(54) BIOSYNTHESIS OF CANNABINOID PRECURSORS USING NOVEL AROMATIC PRENYL TRANSFERASES

(71) Applicant: National University of Singapore, Singapore (SG)

(72) Inventors: Maybelle Darlene Kho Go, Singapore (SG); Kevin Jie Han Lim, Singapore (SG); Yan Ping Lim, Singapore (SG); Wen Shan Yew, Singapore (SG)

(73) Assignee: National University of Singapore, Singapore (SG)

( * ) Notice: Subject to any disclaimer, the term of this patent is extended or adjusted under 35 U.S.C. 154(b) by 553 days.

(21) Appl. No.: 17/767,722

(22) PCT Filed: Oct. 12, 2020

(86) PCT No.: PCT/SG2020/050582
§ 371 (c)(1),
(2) Date: Apr. 8, 2022

(87) PCT Pub. No.: WO2021/071437
PCT Pub. Date: Apr. 15, 2021

(65) Prior Publication Data

US 2024/0084337 A1 Mar. 14, 2024

Related U.S. Application Data

(60) Provisional application No. 62/913,933, filed on Oct. 11, 2019.

(51) Int. Cl.
*C12P 7/42* (2006.01)
*C12N 9/10* (2006.01)
*C12N 15/81* (2006.01)

(52) U.S. Cl.
CPC .............. *C12P 7/42* (2013.01); *C12N 9/1085* (2013.01); *C12N 15/81* (2013.01); *C12Y 205/01039* (2013.01)

(58) Field of Classification Search
CPC ......... C12P 7/42; C12N 9/1085; C12N 15/81; C12Y 205/01039
See application file for complete search history.

(56) References Cited

U.S. PATENT DOCUMENTS

| | | | | |
|---|---|---|---|---|
| 7,361,483 | B2 * | 4/2008 | Kuzuyama | C12N 9/1085 435/193 |
| 8,124,390 | B2 | 2/2012 | Kuzuyama et al. | |
| 11,312,979 | B2 * | 4/2022 | Mookerjee | C12N 9/0006 |
| 2010/0285502 | A1 | 11/2010 | Kuzuyama et al. | |
| 2012/0144523 | A1 | 6/2012 | Page et al. | |
| 2019/0300888 | A1 | 10/2019 | Keasling et al. | |
| 2022/0259603 | A1 * | 8/2022 | Bourgeois | C12P 17/04 |
| 2023/0029027 | A1 * | 1/2023 | Mendez | C12P 7/42 |

FOREIGN PATENT DOCUMENTS

| | | | | |
|---|---|---|---|---|
| CN | 109890202 | A | 6/2019 | |
| JP | 2008-528036 | | 7/2008 | |
| WO | WO-03/014352 | A2 | 2/2003 | |
| WO | WO-2006/081537 | A2 | 8/2006 | |
| WO | WO 2017139496 | A1 | 8/2017 | |
| WO | WO-2017161041 | A1 * | 9/2017 | C12P 17/06 |
| WO | WO-2018148848 | A1 * | 8/2018 | C07C 39/08 |
| WO | WO-2018/209143 | A1 | 11/2018 | |
| WO | WO 2019/014490 | | 1/2019 | |
| WO | WO-2019/014490 | A1 | 1/2019 | |
| WO | WO-2019183193 | A1 * | 9/2019 | A61K 8/97 |
| WO | WO-2021034848 | A1 * | 2/2021 | C12N 15/81 |

OTHER PUBLICATIONS

Koonin EV. Orthologs, paralogs, and evolutionary genomics. Annu Rev Genet. 2005;39:309-38. doi: 10.1146/annurev.genet.39.073003.114725. PMID: 16285863. (Year: 2005).*
Sadowski MI, Jones DT. The sequence-structure relationship and protein function prediction. Curr Opin Struct Biol. Jun. 2009;19(3):357-62. doi: 10.1016/j.sbi.2009.03.008. Epub May 4, 2009. PMID: 19406632. (Year: 2009).*
Seffernick JL, de Souza ML, Sadowsky MJ, Wackett LP. Melamine deaminase and atrazine chlorohydrolase: 98 percent identical but functionally different. J Bacteriol. Apr. 2001;183(8):2405-10. doi: 10.1128/JB.183.8.2405-2410.2001. PMID: 11274097; PMCID: PMC95154. (Year: 2001).*
Tang S, Edwards EA. Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318. PMID: 23479748; PMCID: PMC3638459. (Year: 2013).*
GenBank: SEO62069.1. (Year: 2016).*
Search Report and Written Opinion for Singapore Patent Application No. 112022031898Q, Jan. 29, 2024, 9 pages, Intellectual Property Office of Singapore, Singapore.
Supplemental Partial European Search Report for EP Application No. 20 87 4305, Nov. 15, 2023, 4 pages, European Patent Office, Munich, Germany.
DATABASE GenBnk [online], Accession No. KP893683.1, Jul. 28, 2016, https: https://www.ncbi.nlm.nih.gov/nuccore/KP898683, accessed on Jul. 23, 2024.

(Continued)

*Primary Examiner* — Ganapathirama Raghu
(74) *Attorney, Agent, or Firm* — Cesari and McKenna, LLP

(57) ABSTRACT

A method for producing a cannabinoid precursor by contacting a substrate and geranyl pyrophosphate or farnesyl pyrophosphate with an NphB orthologue. The NphB orthologue is from an organism other than *Cannabis sativa*, and the substrate can be 2,4-dihydroxy-6-pentylbenzoic acid or 2,4-dihydroxy-6-propylbenzoic acid. Also disclosed is a recombinant cell of *Yarrowia lipolytica*, carrying in its genome a nucleic acid encoding an NphB orthologue from an organism other than *Cannabis sativa* such that the NphB orthologue is expressed in the recombinant cell.

8 Claims, 5 Drawing Sheets

Specification includes a Sequence Listing.

(56) References Cited

OTHER PUBLICATIONS

Database: UniProt/TrEMBL[online], Accession No. 0A1H8R5X4_9ACTN, Apr. 12, 2017, https://www.genome.jp/entry/tr:A0A1H8R5X4_9AOTN, accessed on Jul. 23, 2024.
DATABASE UniProt[online], Accession No. A0A0U5C5V3, Mar. 16, 2016, https://www.uniprot.org/uniprotkb/A0A0U5C5V3/entry, accessed on Jul. 23, 2024.
DATABASE UniProt[online], Accession No. S5UCZ5, Oct. 16, 2013, https://www.uniprot.org/uniprotkb/S5UZ5/entry, accessed on Jul. 23, 2024.
DATABASE UniProt[online], Feb. 20, 2007, Accession No. A2AXG5, https://www.uniprot.org/uniprotkb/A2AXG5/entry, accessed on Jul. 23, 2024.
DATABASE UniProt[online], Accession No. G8LVY5, Feb. 22, 2012, https://www.uniprot.org/uniprotkb/G8LVY5/entry, accessed on Jul. 23, 2024.
DATABASE UniProt[online], Accession No. K0EWY8, Nov. 28, 2012, https://www.uniprot.org/uniprotkb/K0EWY8/entry, accessed on Jul. 23, 2024.
Hussain, et al., Identification of Putative Precursor Genes for the Biosynthesis of Cannabinoid-Like Compound in Radula Marginata, Frontiers in Plant Science, May 9, 2018, pp. 1-17.

* cited by examiner

SEQUENCE LISTING

```
<160> NUMBER OF SEQ ID NOS: 8

<210> SEQ ID NO 1
<211> LENGTH: 324
<212> TYPE: PRT
<213> ORGANISM: Streptomyces roseochromogenus subsp. oscitans

<400> SEQUENCE: 1

Met Pro Ala Leu Pro Ile Asp Gln Glu Phe Asp Cys Glu Arg Phe Arg
1               5                   10                  15

Ala Asp Ile Arg Ala Thr Ala Ala Ala Ile Gly Ala Pro Ile Ala His
            20                  25                  30

Arg Leu Thr Asp Thr Val Leu Glu Ala Phe Arg Asp Asn Phe Ala Gln
        35                  40                  45

Gly Ala Thr Leu Trp Lys Thr Thr Ser Gln Pro Gly Asp Gln Leu Ser
    50                  55                  60

Tyr Arg Phe Phe Ser Arg Leu Lys Met Asp Thr Val Ser Arg Ala Ile
65                  70                  75                  80

Asp Ala Gly Leu Leu Asp Ala Ala His Pro Thr Leu Ala Val Val Asp
                85                  90                  95

Ala Trp Ser Ser Leu Tyr Gly Gly Ala Pro Val Gln Ser Gly Asp Phe
            100                 105                 110

Asp Ala Gly Arg Gly Met Ala Lys Thr Trp Leu Tyr Phe Gly Gly Leu
        115                 120                 125

Arg Pro Ala Glu Asp Ile Leu Thr Val Pro Ala Leu Pro Ala Ser Val
    130                 135                 140

Gln Ala Arg Leu Lys Asp Phe Leu Ala Leu Gly Leu Ala His Val Arg
145                 150                 155                 160

Phe Ala Ala Val Asp Trp Arg His His Ser Ala Asn Val Tyr Phe Arg
                165                 170                 175

Gly Lys Gly Pro Leu Asp Thr Val Gln Phe Ala Arg Ile His Ala Leu
            180                 185                 190

Ser Gly Ser Thr Pro Pro Ala Ala His Val Val Glu Glu Val Leu Ala
        195                 200                 205

Tyr Met Pro Glu Asp Tyr Cys Val Ala Ile Thr Leu Asp Leu His Ser
```

-continued

```
    210                 215                 220

Gly Asp Ile Glu Arg Val Cys Phe Tyr Ala Leu Lys Val Pro Lys Asn
225                 230                 235                 240

Ala Leu Pro Arg Ile Pro Thr Arg Ile Ala Arg Phe Leu Glu Val Ala
                245                 250                 255

Pro Ser His Asp Val Glu Glu Cys Asn Val Ile Gly Trp Ser Phe Gly
            260                 265                 270

Arg Ser Gly Asp Tyr Val Lys Ala Glu Arg Ser Tyr Thr Gly Asn Met
        275                 280                 285

Ala Glu Ile Leu Ala Gly Trp Asn Cys Phe Phe His Gly Glu Glu Gly
    290                 295                 300

Arg Asp His Asp Leu Arg Ala Leu His Gln His Thr Glu Ser Thr Met
305                 310                 315                 320

Gly Gly Ala Arg


<210> SEQ ID NO 2
<211> LENGTH: 424
<212> TYPE: PRT
<213> ORGANISM: Aspergillus terreus

<400> SEQUENCE: 2

Met Leu Pro Pro Ser Asp Ser Lys Asp Pro Arg Pro Trp Gln Ile Leu
1               5                   10                  15

Ser Gln Ala Leu Gly Phe Pro Asn Tyr Asp Gln Glu Leu Trp Trp Gln
            20                  25                  30

Asn Thr Ala Glu Thr Leu Asn Arg Val Leu Glu Gln Cys Asp Tyr Ser
        35                  40                  45

Val His Leu Gln Tyr Lys Tyr Leu Ala Phe Tyr His Lys Tyr Ile Leu
    50                  55                  60

Pro Ser Leu Gly Pro Phe Arg Arg Pro Gly Val Glu Pro Glu Tyr Ile
65                  70                  75                  80

Ser Gly Leu Ser His Gly Gly His Pro Leu Glu Ile Ser Val Lys Ile
                85                  90                  95

Asp Lys Ser Lys Thr Ile Cys Arg Leu Gly Leu Gln Ala Ile Gly Pro
            100                 105                 110

Leu Ala Gly Thr Ala Arg Asp Pro Leu Asn Ser Phe Gly Asp Arg Glu
        115                 120                 125

Leu Leu Lys Asn Leu Ala Thr Leu Leu Pro His Val Asp Leu Arg Leu
    130                 135                 140

Phe Asp His Phe Asn Ala Gln Val Gly Leu Asp Arg Ala Gln Cys Ala
145                 150                 155                 160

Val Ala Thr Thr Lys Leu Ile Lys Glu Ser His Asn Ile Val Cys Thr
                165                 170                 175

Ser Leu Asp Leu Lys Asp Gly Glu Val Ile Pro Lys Val Tyr Phe Ser
            180                 185                 190

Thr Ile Pro Lys Gly Leu Val Thr Glu Thr Pro Leu Phe Asp Leu Thr
        195                 200                 205

Phe Ala Ala Ile Glu Gln Met Glu Val Tyr His Lys Asp Ala Pro Leu
    210                 215                 220

Arg Thr Ala Leu Ser Ser Leu Lys Asp Phe Leu Arg Pro Arg Val Pro
225                 230                 235                 240

Thr Asp Ala Ser Ile Thr Pro Pro Leu Thr Gly Leu Ile Gly Val Asp
                245                 250                 255

Cys Ile Asp Pro Met Leu Ser Arg Leu Lys Val Tyr Leu Ala Thr Phe
```

```
            260                 265                 270

Arg Met Asp Leu Ser Leu Ile Arg Asp Tyr Trp Thr Leu Gly Gly Leu
        275                 280                 285

Leu Thr Asp Ala Gly Thr Met Lys Gly Leu Glu Met Val Glu Thr Leu
    290                 295                 300

Ala Lys Thr Leu Lys Leu Gly Asp Glu Ala Cys Glu Thr Leu Asp Ala
305                 310                 315                 320

Glu Arg Leu Pro Phe Gly Ile Asn Tyr Ala Met Lys Pro Gly Thr Ala
                325                 330                 335

Glu Leu Ala Pro Pro Gln Ile Tyr Phe Pro Leu Leu Gly Ile Asn Asp
            340                 345                 350

Gly Phe Ile Ala Asp Ala Leu Val Glu Phe Phe Gln Tyr Met Gly Trp
        355                 360                 365

Glu Asp Gln Ala Asn Arg Tyr Lys Asp Glu Leu Lys Ala Lys Phe Pro
    370                 375                 380

Asn Val Asp Ile Ser Gln Thr Lys Asn Val His Arg Trp Leu Gly Val
385                 390                 395                 400

Ala Tyr Ser Glu Thr Lys Gly Pro Ser Met Asn Ile Tyr Tyr Asp Val
                405                 410                 415

Val Ala Gly Asn Val Ala Arg Val
            420


<210> SEQ ID NO 3
<211> LENGTH: 311
<212> TYPE: PRT
<213> ORGANISM: Streptomyces rubidus

<400> SEQUENCE: 3

Met Pro Gly Ala Ser Lys Thr Glu Ala Val Tyr Ala Ala Ile Glu Glu
1               5                   10                  15

Ala Ser Gly Leu Leu Gly Val Pro Cys Ser Arg Glu Lys Val Gln Gln
            20                  25                  30

Val Leu Gly Ala Phe Gly Glu Gly Val Ser Glu Glu Ser Val Val Val
        35                  40                  45

Leu Ala Met Ala Gly Gly Glu Arg Tyr Arg Gly Asp Ile Asp Tyr Asn
    50                  55                  60

Phe Thr Val Pro Thr Glu Ile Gly Asp Pro Tyr Lys Ile Ala Val Ala
65                  70                  75                  80

Asn Gly Leu Leu Glu Ala Asp Asp His Pro Ala Gly Arg Leu Gly Ala
                85                  90                  95

Asp Ile Ala Glu His Cys Arg Val Ser Phe Phe Gly Val Glu Ala Gly
            100                 105                 110

Val Val Gly Gly Phe Lys Lys Thr Tyr Val Phe Phe Pro Leu Asp Glu
        115                 120                 125

Leu Gly Ser Leu Ser Lys Leu Ala Glu Ile Asp Ser Met Pro Pro Ser
    130                 135                 140

Val Ala Glu His Ala Ala Ala Phe Ala Arg Asn Gly Met Asp Asp Arg
145                 150                 155                 160

Ile Ser Ile Val Gly Ile Asp Tyr Leu Ser Gln Thr Met Asn Val Tyr
                165                 170                 175

Phe Met Ala Ala Pro Val Asp Gln Lys Leu Ala Leu Asp Leu Leu Glu
            180                 185                 190

Asp Leu Glu Leu Pro Ala Pro Ser Pro Asp Leu Leu Glu Phe Ile Pro
        195                 200                 205
```

-continued

Asn Ser Phe Ser Ile Tyr Pro Thr Tyr Ser Trp Asp Ser Ser Gln Ile
210 215 220

Lys Arg Ile Cys Phe Ser Ala Val Ser Pro Asp Gln Ser Ala Tyr Pro
225 230 235 240

Thr Thr Leu His Pro Glu Ile Ala Thr Phe Ala Arg Asn Ala Pro Tyr
245 250 255

Glu Tyr Gly Gly Ala Arg Val Leu Val Tyr Gly Ala Thr Ile Thr Arg
260 265 270

Gly Glu Glu Tyr His Lys Leu Gly Ala Tyr Phe Arg Arg Pro Ala Ala
275 280 285

Phe Trp Asn Ser Leu Pro Leu Ala Ala Thr Phe Glu Arg Leu Ala Ala
290 295 300

Glu Gln Ala Ala Ala Gly Lys
305 310

<210> SEQ ID NO 4
<211> LENGTH: 313
<212> TYPE: PRT
<213> ORGANISM: Aspergillus calidoustus

<400> SEQUENCE: 4

Met Thr Val Ile Glu Pro Pro Ala Pro Val Pro Ile Ala Thr Pro Phe
1 5 10 15

Ser Gln Ser Arg Phe Leu Ser Glu Leu Glu Ser Ala Cys Lys Ala Leu
20 25 30

Asn Thr Ala Tyr Ser Glu Pro Thr Thr Leu Lys Ile Leu Lys Thr Phe
35 40 45

Glu Lys Ser Phe Thr Arg Gly Ala Val Leu Phe Arg Thr Thr Asn Gln
50 55 60

Pro Glu Gly Pro Leu Asn Tyr Arg Val Tyr Glu Arg Gln Ser Ile Asp
65 70 75 80

Met Val Ser Leu Ala Thr Asn Ala Gly Leu Leu Pro Arg Asp Ser Ser
85 90 95

Leu Gly Lys Leu Val Leu Thr Trp Ser Ser Leu Tyr Gly Asn Glu Ser
100 105 110

His Gln Leu Ala Asp Phe Asp Ser Ser Lys Gly Leu Val Lys Phe Trp
115 120 125

Val Phe Leu Gly Gly Ile Arg Pro Leu Asp Glu Ile Leu Asn Val Pro
130 135 140

Gly Val Pro Glu Cys Ile Arg Gly Tyr Arg Gly Met Phe Lys Thr Ile
145 150 155 160

Asn Leu Thr Gly Val Arg His Thr Ala Val Asp Leu Glu Lys Gly Ser
165 170 175

Met Asn Leu Tyr Phe Arg Thr Pro Pro Asp Leu Ser Arg Arg Asp Met
180 185 190

Asp Glu Tyr Ile Ser Leu Ala Gly Ala Asp Pro Leu Pro Asp Ala Leu
195 200 205

Phe Glu Glu Ile His Ala Pro Phe Pro Arg Ala Gly Gly Thr Phe Ala
210 215 220

Val Thr Met Asp Met Thr Thr Gly Arg Ile Ser Arg Val Ala Phe Tyr
225 230 235 240

Ala Leu Arg Leu Glu Glu Asn Asn Pro Pro Ala Ser Ala Val Ser Gly
245 250 255

Arg Ile Lys Thr Phe Phe Glu Val Cys Pro Ser Tyr Asp Pro Asp Glu
260 265 270

Met Lys Ala Leu Ala Trp Ser Phe Gly Glu Gly Asn Lys Arg Tyr Val
275 280 285

Lys Ala Glu His Ser Tyr Thr Gly Asp Leu Val Gly Leu Ile Arg Gly
290 295 300

Trp Gly Thr Ser Met Ser Cys Ala Glu
305 310

<210> SEQ ID NO 5
<211> LENGTH: 305
<212> TYPE: PRT
<213> ORGANISM: Unknown
<220> FEATURE:
<223> OTHER INFORMATION: uncultured bacterium esnapd16.1

<400> SEQUENCE: 5

Met Pro Glu Arg Ser Ala Leu Glu Glu Ile Tyr Ser Ala Ile Asp Thr
1 5 10 15

Thr Ala Arg Val Leu Asp Val Pro Cys Asp Arg Asp Lys Val Gln Pro
20 25 30

Val Leu Asn Ala Tyr Gly Asp Gly Ile Ala Ser Gly Leu Met Val Phe
35 40 45

Thr Met Ala Ala Gly Glu Ser Arg Arg Gly Asp Phe Asp Tyr Asn Phe
50 55 60

Thr Val Pro Ala Asp Gly Pro Asp Pro Tyr Ala Val Ala Val Ala Asn
65 70 75 80

Gly Phe Thr Pro Arg Thr Asp His Pro Val Gly Ser Leu Leu Ser Asp
85 90 95

Ile Ala Glu Arg Ser Pro Leu Gln Phe Tyr Gly Ala Glu Cys Gly Val
100 105 110

Val Glu Gly Phe Lys Lys Thr Tyr Ala Phe Phe Pro Leu Asp Asp Leu
115 120 125

Gln Arg Ala Ser Lys Leu Ala Asp Ile Pro Ser Val Pro Pro Ser Leu
130 135 140

Gly Glu Asn Leu Ser Leu Leu Ala Gly Tyr Gly Leu Asp Asp Asn Val
145 150 155 160

Ser Ile Val Gly Ile Asp Tyr Val His Arg Thr Met Asn Val Tyr Phe
165 170 175

Gly Arg Phe Ser Ala Asp His Ile Glu Pro Gly Thr Val Arg Ser Leu
180 185 190

Leu Arg Asp Ile Gly Met Pro Glu Leu Ser Asp Glu Met Leu Gly Phe
195 200 205

Thr Arg Asn Ala Phe Ser Ile Tyr Pro Thr Phe Ser Trp Asp Ser Pro
210 215 220

Gly Ile Thr Arg Ile Cys Phe Ser Leu Val Thr Gln Asp Pro Arg Ala
225 230 235 240

Leu Pro Ala Val Leu Glu Pro Glu Ile Gly Arg Phe Val Arg Asn Thr
245 250 255

Pro Tyr Ala Tyr Glu Gly Glu Asp Asp Arg Ile Leu Val Tyr Gly Ala
260 265 270

Thr Leu Ser Ala Arg Gly Glu Tyr Trp Lys Ala Gly Val Tyr His Arg
275 280 285

Arg Pro Ala Glu Tyr Trp Ser Lys Val Gln Leu Phe Asp Lys Ile Val
290 295 300

Asn
305

<210> SEQ ID NO 6
<211> LENGTH: 300
<212> TYPE: PRT
<213> ORGANISM: Streptomyces cinnamonensis

<400> SEQUENCE: 6

```
Met Met Ser Gly Thr Ala Asp Leu Ala Gly Val Tyr Ala Ala Val Glu
1               5                   10                  15

Glu Ser Ala Gly Leu Leu Asp Val Ser Cys Ala Arg Glu Lys Val Trp
            20                  25                  30

Pro Ile Leu Ala Ala Phe Glu Asp Val Leu Pro Thr Ala Val Ile Ala
        35                  40                  45

Phe Arg Val Ala Thr Asn Ala Arg His Glu Gly Glu Phe Asp Cys Arg
    50                  55                  60

Phe Thr Val Pro Gly Ser Ile Asp Pro Tyr Ala Val Ala Leu Asp Lys
65                  70                  75                  80

Gly Leu Thr His Arg Ser Gly His Pro Ile Glu Thr Leu Val Ala Asp
                85                  90                  95

Val Gln Lys His Cys Ala Val Asp Ser Tyr Gly Val Asp Phe Gly Val
            100                 105                 110

Val Gly Gly Phe Lys Lys Ile Trp Val Tyr Phe Pro Gly Gly Arg His
        115                 120                 125

Glu Ser Leu Ala His Leu Gly Glu Ile Pro Ser Met Pro Pro Gly Leu
    130                 135                 140

Ala Ala Thr Glu Gly Phe Phe Ala Arg Tyr Gly Leu Ala Asp Lys Val
145                 150                 155                 160

Asp Leu Ile Gly Val Asp Tyr Ala Ser Lys Thr Met Asn Val Tyr Phe
                165                 170                 175

Ala Ala Ser Pro Glu Val Val Ser Ala Pro Thr Val Leu Ala Met His
            180                 185                 190

Arg Glu Ile Gly Leu Pro Asp Pro Ser Glu Gln Met Leu Asp Phe Cys
        195                 200                 205

Ser Arg Ala Phe Gly Val Tyr Thr Thr Leu Asn Trp Asp Ser Ser Lys
    210                 215                 220

Val Glu Arg Ile Ala Tyr Ser Val Lys Thr Glu Asp Pro Leu Glu Leu
225                 230                 235                 240

Ser Ala Arg Leu Gly Ser Lys Val Glu Gln Phe Leu Lys Ser Val Pro
                245                 250                 255

Tyr Gly Ile Asp Thr Pro Lys Met Val Tyr Ala Ala Val Thr Ala Gly
            260                 265                 270

Gly Glu Glu Tyr Tyr Lys Leu Gln Ser Tyr Tyr Gln Trp Arg Thr Asp
        275                 280                 285

Ser Arg Leu Asn Leu Ser Tyr Ile Gly Gly Arg Ser
    290                 295                 300
```

<210> SEQ ID NO 7
<211> LENGTH: 380
<212> TYPE: PRT
<213> ORGANISM: Clostridium clariflavum

<400> SEQUENCE: 7

```
Met Ser Glu Gln Val Cys Glu Ile Leu Trp Ser Lys Lys Met Gln Glu
1               5                   10                  15

Tyr Phe Asn Ser Leu Thr Pro Asn Met Pro Glu Gly Leu Arg Asp Arg
            20                  25                  30
```

Tyr Ile Gly Tyr Val Asn Glu Asn Ala Arg Ala Arg Gly Ala Ser Glu
35 40 45

Val Thr Glu Leu Asp Ile Ile Thr Ala Leu Leu Arg Asn Thr Pro Val
50 55 60

Phe Phe Arg Gln Asn Ile Ser Asn Ile Pro Lys Asp Ile Lys Val Asp
65 70 75 80

Leu Ser Ser Leu Thr Lys Arg Asp Leu Ala Leu Met Ser Asp Asp Ile
85 90 95

Glu Lys Ala Ala Lys Ile Ala Glu Val Gly Cys Asn Lys Glu Leu Val
100 105 110

Asn Lys Ile Leu Asn Val Tyr Glu Glu Gln Phe Ser His Pro Gln Val
115 120 125

Ala Val Ser Phe Arg Thr Thr Thr Lys Pro Val Glu Lys Arg Ser Leu
130 135 140

Asp Val Arg Tyr Val Asp Val Trp Thr Ser His Asp Pro Tyr Ala Met
145 150 155 160

Ala Ile Glu Asn Gly Leu Leu Val Lys Ser Gly His Pro Val Asp Asn
165 170 175

Leu Phe Tyr Asp Ile Lys Ser Asn Phe Pro Ile Met Gly Tyr Gly Val
180 185 190

Asp Phe Gly Val Leu Asn Gly Phe Ala Lys Ile Trp Met Arg Ile Pro
195 200 205

Thr His Leu Pro Val Pro Leu Glu Lys Leu Gln Leu Ile Pro Ser Phe
210 215 220

Pro Asp Ser Leu Lys Asn Tyr Ile Ser Leu Leu Ser Lys Tyr Ser Met
225 230 235 240

Asp Arg Ile Ile Met Val Gly Ile Asp Tyr Ile His Lys Ser Thr Asn
245 250 255

Ile Tyr Phe Val Lys Arg Tyr Tyr Gly Asp Leu Ser Thr Glu Thr Val
260 265 270

Thr Ser Leu Ile Ser Glu Leu Gly Phe Pro Val Pro Ser Asn Glu Leu
275 280 285

Ile Glu Glu Cys Ala His Ala Leu Phe Phe Tyr Cys Thr Phe Thr Trp
290 295 300

Asp Ser Pro Lys Ile Glu Arg Leu Ser Phe His Arg Val Ala His Asp
305 310 315 320

Gln Ser Gln Val Pro Val His Leu His Pro Phe Leu Glu Lys Tyr Ser
325 330 335

Leu Asn Ala Pro Ile Leu Gly Asp Lys Arg Lys Phe Met Tyr Thr Val
340 345 350

Ala Leu Ser Pro Lys Gly Asn Tyr Ile Lys Leu Glu Ser Asp Tyr Ser
355 360 365

Ser Gly Ile Met Ala Asp Ala Leu Val Glu Thr Tyr
370 375 380

<210> SEQ ID NO 8
<211> LENGTH: 292
<212> TYPE: PRT
<213> ORGANISM: Nocardia brasiliensis

<400> SEQUENCE: 8

Met Thr Leu Asp Asn Leu Arg Arg Asp Leu Arg Glu Tyr Ala Arg Leu
1 5 10 15

Ala Glu Val Gly Tyr Asp Pro Ala Val Val Asp Pro Val Leu Glu Pro

-continued

```
            20                  25                  30

Leu Ala Asp Leu Trp Thr Asn Ser Val Val Ala Val Arg Thr Thr Thr
        35                  40                  45

His Pro Val Pro Glu Arg Asp Val Asn Val Arg Leu Met His Ala Gly
    50                  55                  60

Glu Pro Thr Gly Leu Val Thr Thr Leu Arg Asp Ala Gly Leu Ile Thr
65                  70                  75                  80

Tyr Thr Gly His Pro Met Glu Glu Leu Leu Ala Ala Val Ser Ala Ala
                85                  90                  95

Val Pro Ala Arg Ala Gly Val Asp Val Ala Leu Ser Glu Gly Val Gln
            100                 105                 110

Lys Ile Trp Leu Ile Phe Pro Glu Leu Leu Ser Val Glu Arg Met Leu
        115                 120                 125

Ala Phe Pro Gly Val Pro Glu Ala Ala Arg Ala His Ala Ala His Leu
    130                 135                 140

Ser Arg Tyr Gly Gly Arg Ile Gly Ile Leu Ala Val Asp Phe Ala Ala
145                 150                 155                 160

Arg Thr Met Asn Leu Tyr Ser Asn Val Phe Glu Pro Gly Ser Leu Gly
                165                 170                 175

Ser Ala Asp Ile Ala Glu Ile Leu Ala Asp Leu Asp Phe Thr Ala Ala
            180                 185                 190

Thr Glu Glu Glu Leu Ala Leu Leu Gly Arg Thr Phe Asn Ile Tyr Arg
        195                 200                 205

Thr Phe Ser Trp Thr Ser Ala Arg Met Gln Arg Ile Cys Phe Pro Leu
    210                 215                 220

Arg Val Gln Ala Ala Asn Phe Pro Ala His Leu His Pro Val Leu Ala
225                 230                 235                 240

Arg Phe Val Glu Gly Ala Pro Phe Val Asp Pro Asp Thr Arg Gly Phe
                245                 250                 255

Val Phe Tyr Ala Ala Tyr Gly Pro Thr Asp Arg Tyr Tyr Lys Val Gln
            260                 265                 270

Ala Glu Tyr Ala Thr Gly Gln Pro Val Thr Phe Pro Gly Gly Thr Ala
        275                 280                 285

Pro Arg Val Asn
    290
```

BIOSYNTHESIS OF CANNABINOID PRECURSORS USING NOVEL AROMATIC PRENYL TRANSFERASES

CROSS-REFERENCE TO RELATED APPLICATIONS

The present application is the National Stage of International Application No. PCT/SG2020/050582, filed on Oct. 12, 2020, which claims the benefit of U.S. Provisional Patent Application Ser. No. 62/913,933, filed on Oct. 11, 2019. The Content of both applications is hereby incorporated by reference in its entirety.

BACKGROUND

The structure and function of an aromatic prenyl transferase (NphB) from *Streptomyces* sp. strain CL190 has been elucidated. See Kumano et al., Bioorg. Med. Chem. 2008, 16 (17): 8117-26. Previous studies reported in Zirpel et al., J. Biotechnol. 2017, 259:204-212, showed that NphB was able to utilize the same substrates as the membrane-bound geranylpyrophosphate: olivetolate geranyltransferase from the *Cannabis* plant to form the cannabinoid precursor cannabigerolic acid (CBGA).

CBGA is commonly known as the first branch point of the cannabinoid biosynthetic pathway found in the *Cannabis* plant, and wild-type NphB can make CBGA, as well as an O-prenylated side product, i.e., 2-O-geranyl olivetolic acid.

Further enzymes and methods are needed for synthesizing known cannabinoid precursors and novel cannabinoid precursors with specificity and high yield.

SUMMARY

A method is disclosed for producing a cannabinoid precursor. The method includes the steps of contacting a substrate and geranyl pyrophosphate or farnesyl pyrophosphate with an NphB orthologue. The substrate can be, e.g., 2,4-dihydroxy-6-pentylbenzoic acid or 2,4-dihydroxy-6-propylbenzoic acid, and the NphB orthologue is from an organism other than *Cannabis sativa.*

Also provided is a recombinant cell of *Yarrowia lipolytica*, carrying in its genome a nucleic acid encoding an NphB orthologue. The NphB orthologue, which is from an organism other than *Cannabis sativa*, is expressed in the recombinant cell.

The details of one or more embodiments are set forth in the description and the examples below. Other features, objects, and advantages will be apparent from the detailed description, from the drawings, and also from the appended claims.

BRIEF DESCRIPTION OF THE DRAWINGS

The invention description below refers to the accompanying drawings, of which.

DETAILED DESCRIPTION

Figure 1:
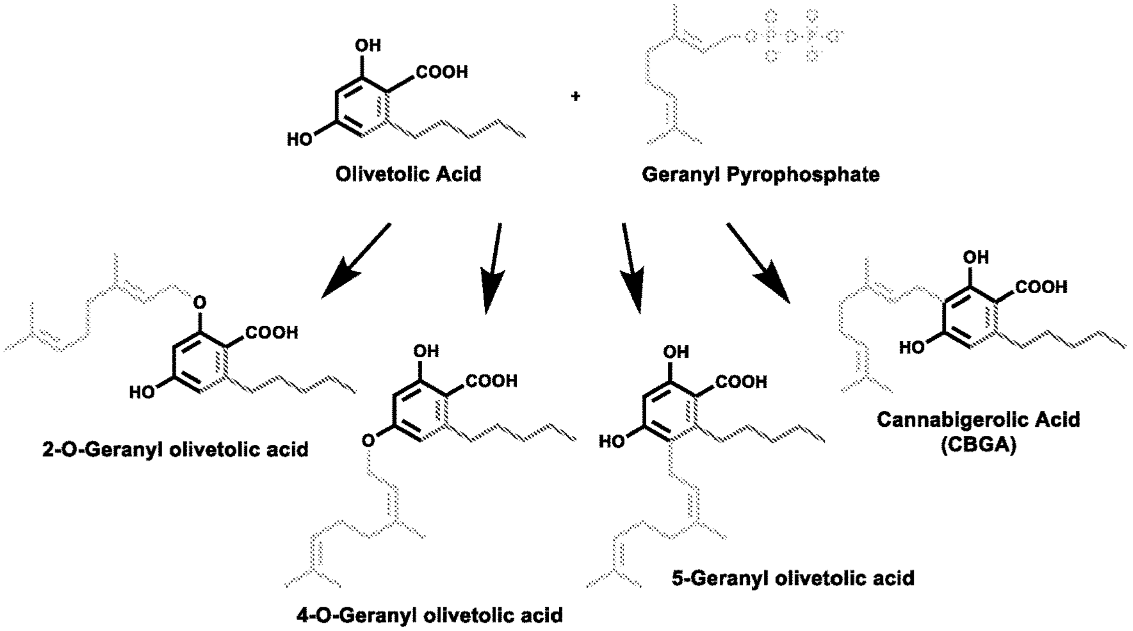
FIG. 1 shows the structures of cannabinoid products using olivetolic acid and geranyl pyrophosphate as substrate. The molecular formula and formula weight of all the possible products are $C_{22}H_{31}O_4$ and 359.22, respectively. Black: part of olivetolic acid which is derived from three units of malonyl-CoA; Dark Gray: part of olivetolic acid derived from hexanoyl-CoA; Light Gray: part of geranyl pyrophosphate which is transferred by the orthologues.

Disclosed are enzymes that catalyze the biosynthesis of cannabinoid precursors by transferring isoprene units from certain pyrophosphates, e.g., geranyl pyrophosphate, to aromatic polyketides such as 2,4-dihydroxy-6-pentylbenzoic acid, i.e., olivetolic acid, and 2,4-dihydroxy-6-propylbenzoic acid. These enzymes, from organisms other than *Cannabis sativa*, can be recombinantly expressed in *Escherichia coli* or *Yarrowia lipolytica* and subsequently employed for their prenyl transferase activity.

As summarized above, a method for producing a cannabinoid precursor is disclosed. In a specific example, the substrate is olivetolic acid, the pyrophosphate is geranyl pyrophosphate, and the cannabinoid precursor produced has a mass to charge ratio of 359.22 and a retention time of longer than 6.1 minutes, as determined by LC/MS analysis. The cannabinoid precursor described herein also falls within the scope of the invention.

In the above method, the source of the NphB orthologue can be, but is not limited to, *Streptomyces* roseochromogenus subsp. *oscitans, Streptomyces rubidus, Streptomyces cinnamonensis, Aspergillus calidoustus, Aspergillus terreus, Clostridium clariflavum, Nocardia brasiliensis*, and uncultured bacterium esnapd16.1.

In a particular aspect of the method, the NphB orthologue has the amino acid sequence of any one of SEQ ID NOs: 1-8. Alternatively, the NphB orthologue can have an amino acid sequence at least 70% identical (e.g., at least 70%, 75%, 80%, 85%, 90%, 95%, and 99%) to any one of SEQ ID NOs: 1-8 and has aromatic prenyl transferase activity.

In an exemplary method, the NphB orthologue is a recombinant enzyme. The recombinant enzyme can be produced in, e.g., *Escherichia coli* and *Yarrowia lipolytica.*

Also mentioned above is a recombinant cell of *Yarrowia lipolytica*, including in its genome a nucleic acid encoding an NphB orthologue. The NphB orthologue is from an organism other than *Cannabis sativa.*

Exemplary sources of the NphB orthologue are *Streptomyces* roseochromogenus subsp. *oscitans, Streptomyces rubidus, Streptomyces cinnamonensis, Aspergillus calidous-*

*tus, Aspergillus terreus, Clostridium clariflavum, Nocardia brasiliensis*, and uncultured bacterium esnapd16.1.

In a particular recombinant cell, the NphB orthologue has the amino acid sequence of any one of SEQ ID NOs: 1-8. In another example, the NphB orthologue can have an amino acid sequence at least 70% identical (e.g., at least 70%, 75%, 80%, 85%, 90%, 95%, and 99%) to any one of SEQ ID NOs: 1-8 and has aromatic prenyl transferase activity.

Without further elaboration, it is believed that one skilled in the art can, based on the disclosure herein, utilize the present disclosure to its fullest extent. The following specific example is, therefore, to be construed as merely descriptive, and not limitative of the remainder of the disclosure in any way whatsoever. All publications cited herein are incorporated by reference in their entirety.

EXAMPLE

Through a search of available sequence databases, 105 gene orthologues to NphB were identified that were also annotated in the UniProt® database as potential aromatic prenyl transferases. The genes were synthesized and cloned into a modified pES2 vector containing a T7 promoter and terminator. The vectors were transformed into *Escherichia coli* Acella™ cells using chemical treatment and grown on LB+ streptomycin selection plates at 37° C. Sequence-verified clones were picked and grown in LB+ streptomycin media until an $OD_{600nm}$ of 0.8. Protein expression was induced by adding 0.1 mM IPTG to the cultures and incubating at 25° C. for 24 h. The cells were subsequently harvested and stored at −20° C. until protein purification.

Pelleted cells were resuspended in 100 μL of binding buffer containing 20 mM Tris-HCl (pH 7.9), 500 mM NaCl, and 5 mM imidazole. The cells were subsequently lysed by sonication and the cell debris was removed by centrifugation for 30 min. at 4° C. The supernatant containing His-tagged proteins was purified using $Ni^{2+}$ affinity chromatography and the recombinant proteins were eluted with buffer containing 20 mM Tris-HCl (pH 7.9), 500 mM NaCl, and 100 mM L-histidine. The concentration of His-tagged proteins was estimated using an ELISA detection kit, and the purified NphB orthologues were stored at 4° C.

The NphB orthologues were tested for prenyl transferase using an in vitro prenyl transferase assay. In a reaction volume of 200 μL, 20 μL of 1 M Tris-HCl (pH 7.9), 2 μL of 1 M $MgCl_2$, 4 μL of 50 mM aromatic polyketide substrate, e.g., olivetolic acid and divarinic acid, 20 μL of 10 mM geranyl pyrophosphate, and 50 μg of purified NphB orthologues were combined and incubated at 30° C. A control reaction without enzyme was also prepared.

After 24 h, the reaction mixture was acidified to pH 3.0 with 6 M HCl and extracted with ethyl acetate three times. The samples were dried under vacuum and redissolved in methanol for LC-MS analysis using the negative ion mode. Extracted-ion-chromatograms (EIC) for m/z=359.22 (if olivetolic acid is used) and m/z=331.19 (if divarinic acid is used) were generated for each sample to determine if the biosynthesis of a potential cannabinoid precursor was catalyzed by the NphB orthologue. The structures of potential cannabinoid precursors that can be biosynthesized using olivetolic acid and geranyl pyrophosphate as substrates are shown in FIG. 1.

Figure 2:
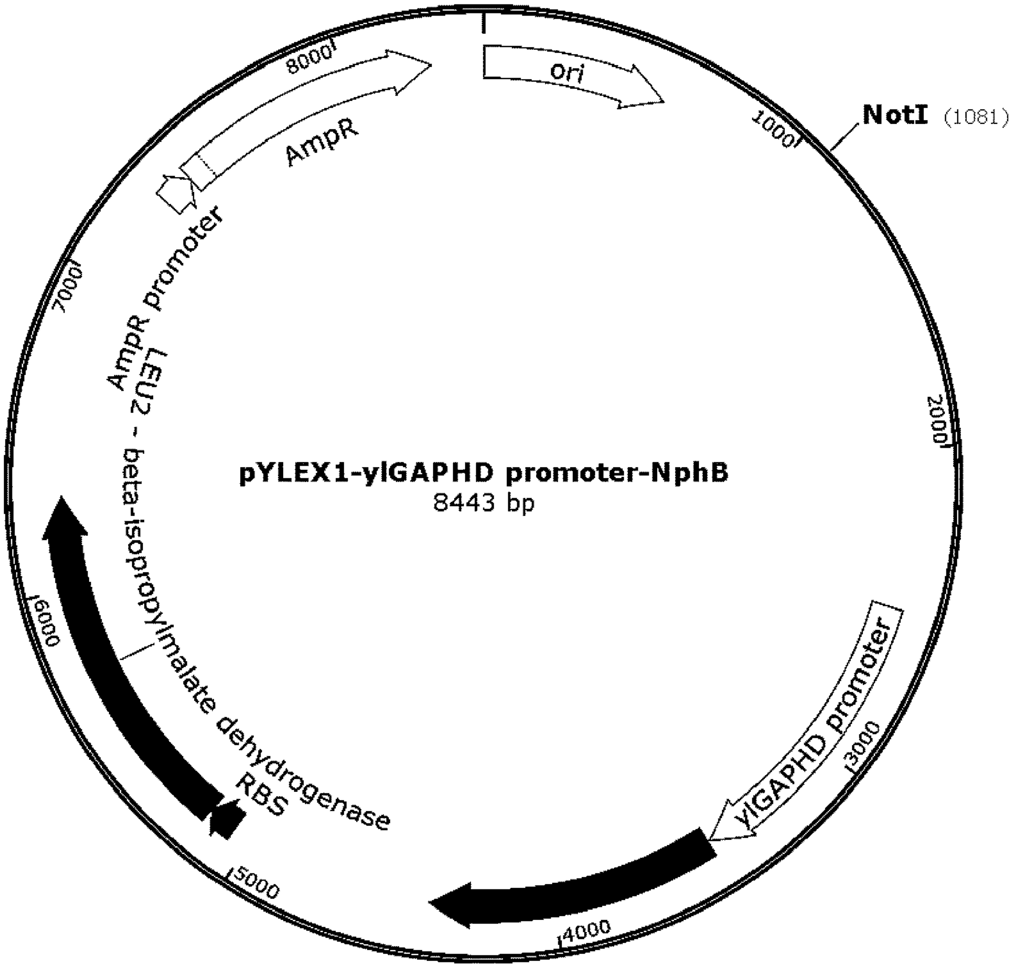
FIG. 2 is a diagram of the pYLEX1 vector used to integrate genes encoding NphB orthologues into the *Y. lipolytica* genome.

Certain orthologues of NphB produced a novel product, identified as a new peak in LC-MS analysis compared to the peaks formed by wild-type NphB. Particular orthologues also demonstrated a greater yield of CBGA. Such orthologues are selected for subsequent cloning into *Yarrowia lipolytica*. They are subcloned into a modified pYLEX1 vector (Yeastern Biotech; see FIG. 2) and transformed into *Y. lipolytica* using chemical treatment. Transformants are selected on YNB agar without leucine and used for subsequent yield optimization assays.

Out of 105 orthologues tested, eight orthologues showed good protein expression and novel prenyl transferase activities. The eight orthologues are listed in Table 1 below, together with corresponding UnipProt® ID and source organism.

TABLE 1

NphB orthologues having novel prenyl transferase activity.

| UniProt ® ID | Orthologue | Organism | % identity to NphB | SEQ ID NO: |
|---|---|---|---|---|
| Q8GHB2 | P3A5 | *Streptomyces roseochromogenus* subsp. *oscitans* | 14.3 | 1 |
| A0A1B0UHJ4 | Y1C5 | *Aspergillus terreus* | 11.7 | 2 |
| A0A1H8R5X4 | P3E8 | *Streptomyces rubidus* | 36.2 | 3 |
| A0A0U5C5V3 | P3E2 | *Aspergillus calidoustus* | 14.0 | 4 |
| S5UCZ5 | 1BF1 | uncultured bacterium esnapd16.1 | 33.8 | 5 |
| A2AXG5 | P3A6 | *Streptomyces cinnamonensis* | 35.7 | 6 |
| G8LVY5 | P3F5 | *Clostridium clariflavum* | 25.4 | 7 |
| K0EWY8 | 1BC2 | *Nocardia brasiliensis* | 16.1 | 8 |

P3E8 had a comparable yield of CBGA compared to wild-type NphB, and all eight orthologues showed at least one new peak in LC-MS analysis which also had a molecular formula of $C_{22}H_{31}O_4$ (FW=359.22).

Figure 3A:
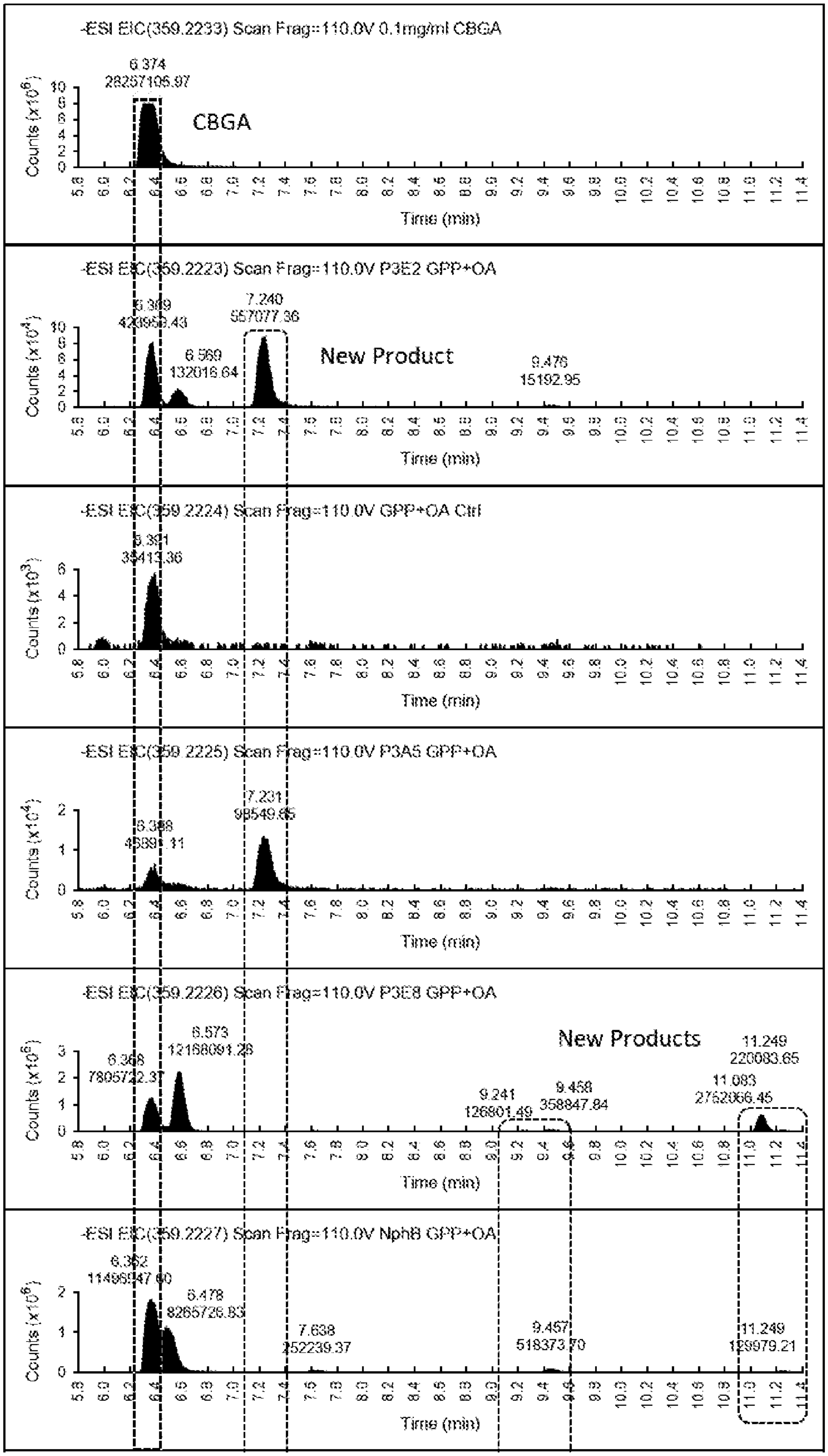
FIG. 3A shows LC-MS spectra of cannabinoid precursors having m/z=359.22 biosynthesized from three NphB orthologues: row 1=CBGA standard, row 2=P3E2, row 3=no enzyme negative control, row 4=P3A5, row 5=P3E8, row 6=NphB positive control, row 7=1BF1, row 8=Y1C5. Peaks are identified by retention times and relative area under the peak.
Figure 3A:
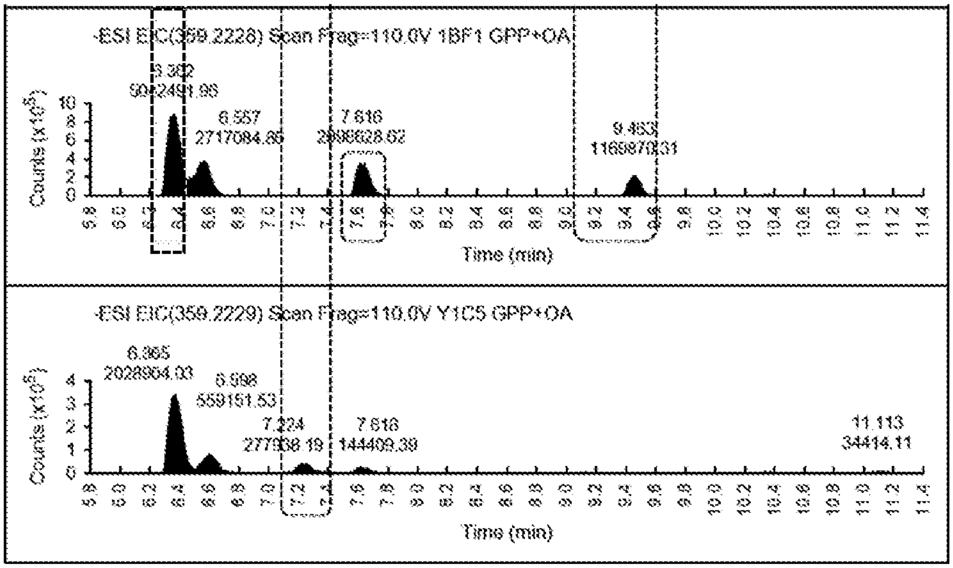
Figure 3B:
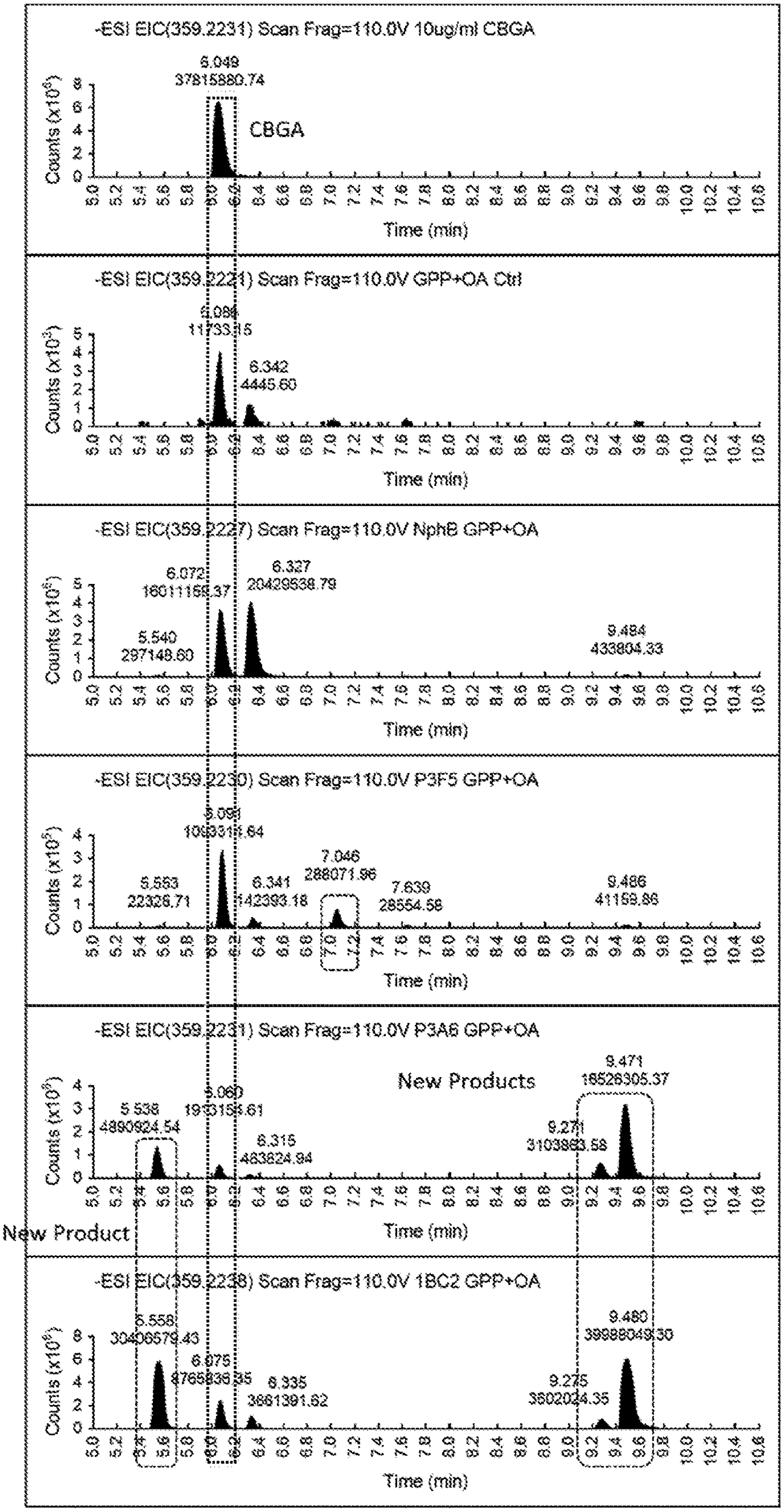
FIG. 3B shows LC-MS spectra of cannabinoid precursors having m/z=359.22 biosynthesized from three additional NphB orthologues: row 1=10 μg/ml CBGA standard, row 2=no enzyme negative control, row 3=NphB positive control, row 4=P3F5, row 5=P3A6, row 6=1BC2. Peaks are identified by retention times and relative area under the peak.

As shown in FIGS. 3A and 3B, all eight orthologues, as well as wild-type NphB, can produce CBGA (retention time: 6.4 min. in FIG. 3A and 6.1 min. in FIG. 3B). All orthologues except for P3A5 also produced a side product, i.e., 2-O-geranyl olivetolic acid (retention time: 6.6 min. in FIG. 3A and 6.3 min. in FIG. 3B). Orthologues P3A5, Y1C5, and P3E2 each produced significant amounts of a new prenylated product with m/z=359.2225 at a retention time of 7.23-7.24 min. that was not observed in the reaction using wild-type NphB.

Novel products having m/z=359.22 and identified in FIGS. 3A and 3B are summarized in Table 2 below. These products have retention times not seen for those produced with the wild-type NphB enzyme.

TABLE 2

| Novel products produced by orthologues from geranyl pyrophosphate and olivetolic acid | |
|---|---|
| Orthologue | Retention time(s) in min. |
| P3E2 | 7.24 |
| P3A5 | 7.23 |
| P3E8 | 9.24, 11.08 |
| 1BF1 | 7.62, 9.46 |
| Y1C5 | 7.22, 7.62 |
| P3F5 | 7.05 |
| P3A6 | 5.54, 9.27, 9.47 |
| 1BC2 | 5.56, 9.28, 9.48 |

A study showed that two orthologues, corresponding to UnipProt® IDs: C4PWA1 and Q9L9F1, produced only trace amounts of new prenylated products, suggesting that these orthologues had prenylated the olivetolic acid at a site different from wild-type NphB.

Figure 4:
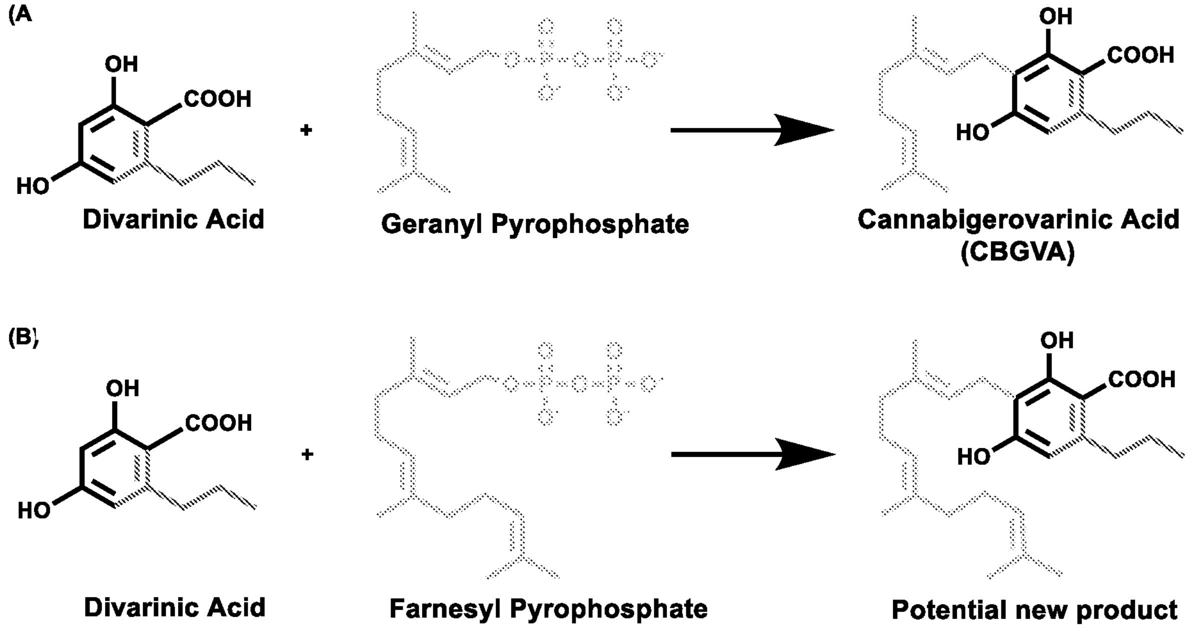
FIG. 4 shows the structures of potential cannabinoid products biosynthesized using divarinic acid (top row), which has two fewer carbon units compared to olivetolic acid, resulting in the production of CBGVA, which is two carbons shorter than CBGA, or using farnesyl pyrophosphate (bottom row) instead of geranyl pyrophosphate resulting in the production of a novel cannabinoid precursor.

In addition, different substrates can be incubated with the NphB orthologues to determine if novel cannabinoid precursors can be produced. FIG. 4 shows the potential product that can be formed when either olivetolic acid or geranyl pyrophosphate, or both, are replaced. Novel cannabinoid precursors can then be tested with downstream cannabinoid synthases in order to diversify cannabinoid compound libraries.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for producing a cannabinoid precursor, the method comprising contacting 2,4-dihydroxy-6-pentylbenzoic acid (olivetolic acid) and geranyl pyrophosphate with an NphB orthologue comprising the amino acid sequence of any one of SEQ ID NOs: 1-8 to produce cannabigerolic acid (CBGA) and at least one other product having a same molecular formula as CBGA and a longer retention time than CBGA as determined by liquid chromatography mass spectrometryl.

2. The method of claim 1, further comprising producing the NphB orthologue as a recombinant enzyme in *Yarrowia lipolytica.*

3. The method of claim 1, wherein the NphB orthologue is from *Streptomyces* roseochromogenus subsp. *oscitans, Streptomyces rubidus, Streptomyces cinnamonensis, Aspergillus calidoustus, Aspergillus terreus*, or *Clostridium clariflavum, Nocardia brasiliensis.*

4. The method of claim 1, wherein the NphB orthologue has the amino acid sequence of SEQ ID NOs: 1 or 2.

5. The method of claim 1, wherein the NphB orthologue has the amino acid sequence of SEQ ID NOs: 1, 3-6, or 8.

6. The method of claim 1, wherein the NphB orthologue has the amino acid sequence of SEQ ID NOs: 1, 3-5, or 8.

7. The method of claim 1, wherein the NphB orthologue has the amino acid sequence of SEQ ID NOs: 3-5 or 8.

8. The method of claim 1, wherein the NphB orthologue has the amino acid sequence of SEQ ID NO: 3.

* * * * *